US006287280B1

(12) United States Patent
Lampropoulos et al.

(10) Patent No.: US 6,287,280 B1
(45) Date of Patent: *Sep. 11, 2001

(54) HEMOSTASIS VALVE APPARATUS WITH INTEGRAL INTRODUCER

(75) Inventors: Fred P. Lampropoulos, Sandy; Brian W. Stevens, Pleasant Grove, both of UT (US)

(73) Assignee: Merit Medical Systems, Inc., South Jordan, UT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/390,822

(22) Filed: Sep. 7, 1999

(51) Int. Cl.[7] .................................................. A61M 5/178
(52) U.S. Cl. ............................. 604/167.03; 604/165.01; 604/256; 604/246
(58) Field of Search ........................... 604/246, 164.01, 604/164.02, 165.01, 167.01, 167.02, 167.03, 167.04, 167.06, 256

(56) References Cited

U.S. PATENT DOCUMENTS

| 3,585,996 | 6/1971 | Reynolds ........................ 128/214.4 |
|---|---|---|
| 4,610,469 | 9/1986 | Wolff-Mooij ...................... 285/260 |
| 4,935,010 | 6/1990 | Cox et al. ........................ 604/122 |
| 5,009,391 | 4/1991 | Steigerwald .................... 251/149.1 |
| 5,059,186 | 10/1991 | Yamamoto et al. ................ 604/280 |
| 5,062,836 | 11/1991 | Wendell ............................ 604/167 |
| 5,167,636 * | 12/1992 | Clement ............................. 604/167 |
| 5,195,980 | 3/1993 | Catlin ................................ 604/167 |
| 5,324,271 * | 6/1994 | Abiuso et al. ..................... 604/167 |
| 5,334,160 | 8/1994 | Ellis .................................. 604/167 |
| 5,376,077 | 12/1994 | Gomringer ......................... 604/167 |
| 5,405,323 * | 4/1995 | Rogers et al. ....................... 604/53 |
| 5,591,137 | 1/1997 | Stevens .............................. 604/256 |
| 5,651,170 | 7/1997 | Stevens .............................. 29/450 |
| 5,676,671 | 10/1997 | Inoue ................................ 606/108 |
| 5,693,025 | 12/1997 | Stevens .............................. 604/167 |
| 5,766,151 * | 6/1998 | Valley et al. ........................ 604/96 |
| 5,935,112 * | 8/1999 | Stevens et al. .................... 604/256 |
| 5,971,958 * | 10/1999 | Zhang ................................ 604/164 |

OTHER PUBLICATIONS

Endovascular Therapy Daily No. 4, *Bifurcation Day: Does Stenting Resolve All Problems?*, May 8, 1998.
Product Brochure for Guidant Corporation; *CoPilot Bleedback Control Valve*, Copyright 1999.

* cited by examiner

*Primary Examiner*—Richard K. Seidel
*Assistant Examiner*—Jennifer Maynard
(74) *Attorney, Agent, or Firm*—Workman, Nydegger & Seeley (57) ABSTRACT

A valve system configured to access the cardiovascular system of a patient includes: (i) a valve body having a lumen therethrough; (ii) a selectively openable resilient first seal, (iii) a compressible second seal including an opening which communicates with the lumen when the second seal is in an open position; (iii) a locking nut movably coupled to the valve body, the locking nut configured to selectively increase and decrease compressive force on the second seal; and (iv) an introducer configured to selectively open the resilient first seal. The introducer has a proximal end and a distal end. The introducer is movably coupled to the locking nut and reciprocates between a first position and a second position within the locking nut. The resilient first seal is in the closed position when the introducer is in the first position and the resilient first seal is in the open position when the introducer is in the second position. The introducer protects elongate instruments such as catheters having stents thereon while the instruments are moved through the resilient seal while the seal is opened by the introducer.

19 Claims, 6 Drawing Sheets

HEMOSTASIS VALVE APPARATUS WITH INTEGRAL INTRODUCER

BACKGROUND OF THE INVENTION

1. The Field of the Invention

The present invention relates to valves. More particularly, this application relates to hemostasis valves for use in medical procedures.

2. Relevant Technology

Various medical procedures require temporary and often repeated introduction and removal of catheters and/or guide wires within the cardiovascular system of a patient. For example, using only a relatively small incision, a catheter can be introduced into a blood vessel of a patient and used to implant a stent or deliver a fluid directly to a predetermined location within the cardiovascular system. Catheters can also be used for exploratory surgery and for removing tissue samples within a patient's body.

Operations using catheters can often require the insertion and removal of several different types of catheters and guide wires, which can be employed to guide catheters to a desired location within the body. One of the problems encountered with the insertion, removal and adjustment of catheters and guide wires is controlling bleeding at the point where the catheters and guide wires are first introduced into the cardiovascular system.

In one approach to controlling bleeding and ensuring easy insertion and removal of the catheter and/or guide wire within the cardiovascular system, one end of a hollow introducer is first secured within a large blood vessel of a patient. The opposite end of the introducer is positioned outside the body of the patient and is attached to an adapter.

Such an adapter typically comprises a short, rigid tube having a passageway extending therethrough. Attached at one end of the adapter tube is a connector. The connector is used to connect the passageway of the adapter tube to the exposed end of the introducer. This enables fluids and/or medical instruments, such as catheters and guide wires, to pass between the adaptor tube and the introducer.

Positioned at the opposite end of the adaptor tube from the connector is a valve commonly referred to as a hemostasis valve. The hemostasis valve typically includes a seal positioned within a valve body. During use of the adaptor, the pressure of the blood of the patient caused by the beating of the patient's heart can cause blood from the patient to flow through the introducer and into the passageway of the adaptor tube. The seal is designed to prevent blood from escaping out of the adaptor.

One typical hemostasis valve is a "slit" valve. Another typical hemostasis valve is known as a "Touhy Borst" valve. Such a valve typically includes an elastomeric membrane having a passageway therethrough through which a catheter can extend. The elastomeric membrane can be selectively compressed about the exterior surface of a catheter to thereby establish hemostasis.

One increasingly common use for catheters is in the strategic placement of small balloons that can be selectively inflated within a blood vessel. The balloons are used for opening blood vessels that have been blocked or partially blocked by fat build-up. This opening or altering of the blood vessel is referred to as angioplasty.

Sometimes during angioplasty an expandable stent is mounted on a balloon catheter. The stent/balloon catheter assembly is guided through an adaptor into a blood vessel until reaching a particular portion of the vessel. Upon reaching the desired location, the balloon is inflated, thereby expanding the stent. The balloon is then deflated, separating the balloon from the expanded stent. The stent then remains in the blood vessel, thereby retaining the blood vessel in an expanded position, and the balloon catheter is removed from the blood vessel.

Stents may have a variety of different designs and may be implanted into blood vessels through a variety of different methods. Typically, stents are initially inserted through an adaptor, then inserted further into the blood vessel.

During such insertion, the stents are inserted through the hemostasis valve of the adaptor. However, unprotected stents are often damaged by the tortuous path travelled when pushed through a hemostasis valve. Stents, which are often relatively delicate, malleable structures, may snag on the valve or may be otherwise blocked or damaged by the valve. Unprotected balloons and stents can be caught in typical hemostasis valves and can thereby become dislodged or deformed.

According to one method for protecting a stent while inserting the stent through a hemostasis valve, the stent is placed within a catheter which is then inserted through the hemostasis valve and further into the cardiovascular system of the patient. However, this typically requires the use a separate catheter.

According to another method for protecting a stent, the hemostasis valve is first removed from the adaptor. The stent is then placed in the adaptor body and the valve is threaded back onto the adaptor behind the stent. This approach, however, is cumbersome and can result in the contents of the hemostasis valve being spilled during a medical procedure.

According to another method, an integral introducer is movably coupled within the valve and selectively opens a slit valve. However, such valves are typically designed to apply a set, predetermined amount of sealing pressure on a particular elongate instrument in an attempt to establish hemostasis. If the practitioner desires to increase or decrease the sealing pressure on a catheter or other instrument, the practitioner is required to employ a different valve which has a tighter or looser seal. This may require the practitioner to purchase and store a number of different valves for use during a particular procedure or with catheters having varying sizes.

There is therefore a need in the art for an improved hemostasis valve which enables an instrument to be protected while passing through the valve. There is also a need in the art for a hemostasis valve which does not limit a practitioner to a set, predetermined amount of sealing pressure which the practitioner can apply to a particular elongate medical instrument.

SUMMARY AND OBJECTS OF THE INVENTION

It is therefore an object of the present invention to provide an improved hemostasis valve.

It is another object of the present invention to provide an improved hemostasis valve which minimizes the loss of body fluids during insertion, repositioning, or removal of medical instruments, such as catheters and guide wires, from the hemostasis valve.

It is a further object of the present invention to provide an improved hemostasis valve having an integral, movably coupled introducer.

It is another object of the present invention to provide an improved hemostasis valve that is capable of being opened to allow an instrument to pass therethrough while protecting the instrument and without requiring the valve to be removed from the adaptor.

It is yet another object of the present invention to provide an improved hemostasis valve that includes a compression seal which allows the hemostasis valve to be sealed while still allowing a catheter or guide wire to be longitudinally positioned therethrough.

Still another object of the present invention is to provide an improved hemostasis valve that allows the insertion, repositioning or removal of a catheter or guide wire with increased speed and substantially without the loss of body fluids.

Still another object of the invention is to provide a hemostasis valve having both a resilient seal and a compressible seal, wherein the resilient seal is selectively opened by an integral introducer.

Still another object of the invention is to provide a hemostasis valve having a selectively compressible seal which can be adjusted for differently sized catheters and to apply a desired amount of seal.

Still another object of the invention is to provide a hemostasis valve which can be selectively adjusted in order to prevent the movement of a catheter in and out of the valve.

Still another object of the invention is to provide a hemostasis valve having an introducer for protecting elongate medical instruments and which can be adjusted by a practitioner to apply a desired amount of sealing pressure on an elongate member.

A hemostasis valve of the present invention is adapted for accessing the cardiovascular system of a patient. The hemostasis valve has a valve body, a compressible seal, an integral, movable introducer, and preferably, a resilient seal.

When a compressive force is exerted on the compressible seal, a portion of the compressible seal moves radially inward to form a progressively tighter seal. A hollow, rotating locking nut threadably coupled to the valve body is employed to adjustable exert the desired amount of compressive force. The amount of compressive force that is being exerted on the compressible seal can be incrementally adjusted through selective rotation of the nut. The introducer is movably coupled within the rotating nut.

In a preferred embodiment, a resilient seal is located proximally from the compressible seal and is selectively opened by the introducer. Upon moving the introducer from a first position to a second position within the valve, the introducer opens the normally closed resilient seal. An elongate instrument, such as a balloon catheter or stent assembly can then be inserted through the introducer and past the resilient seal without being damaged by the seal. Upon removing the introducer, the resilient seal seals about the exterior surface of the elongate instrument and prevents the flow of fluid from the valve.

A variety of other advantages are also achieved in the present invention. First, the compressible seal can be selectively adjusted to accommodate catheters having a variety of different diameters. Second, the amount of sealing pressure can be adjusted to prevent an elongate member from being inadvertently moved into or out of the valve or to allow the elongate member to move while simultaneously substantially preventing blood loss. Third, the resilient seal can seal against an elongate member while the compressible seal is open, e.g., during adjustment of the position of the elongate member.

Finally, in the preferred embodiment, the introducer selectively slides through the rotating locking nut between the first and second position to open the resilient seal. This design elegantly combines the advantages of an adjustable, compressible seal and an integral, sliding introducer.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The present invention relates to an improved valve apparatus that minimizes the loss of body fluids during insertion, repositioning or removal of elongate medical instruments, such as catheters and guide wires, from the hemostasis valve. The valve apparatus is preferably incorporated into an adaptor.

Figure 1:
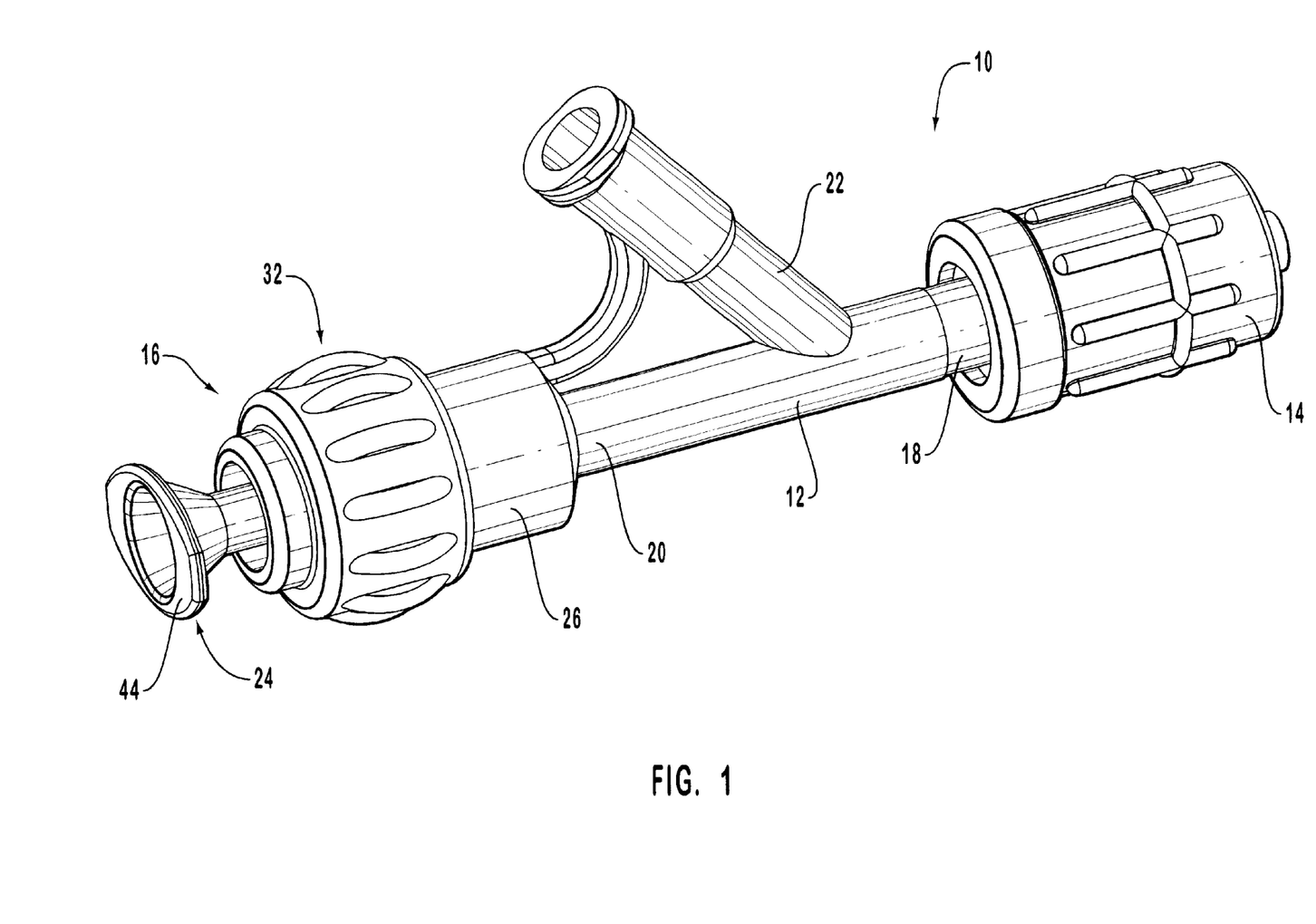
FIG. 1 is a perspective view of an adaptor of the present invention having a valve apparatus of the present invention.

With reference now to FIG. 1, an embodiment of the present invention is shown. FIG. 1 depicts an adaptor 10 comprising a tubular body 12, a rotatable connector 14, and a valve apparatus 16 of the present invention. Hollow tubular body 12 has a distal end 18 and an opposing proximal end 20. Rotatable connector 14 is positioned at distal end 18 of tubular body 12. Rotatable connector 14 is an example of means for coupling body 12 in fluid communication with an introducer (not shown) positioned at least partially within a patient's body. Valve apparatus 16 is positioned at proximal end 20 of tubular body 12 and is configured to provide access to the cardiovascular system of a patient.

An optional embodiment of adaptor 10, as shown in FIG. 1, includes a supplemental access tube 22 attached to tubular body 12. Supplemental access tube 22 has a central bore formed therethrough so as to be in fluid communication with tubular body 12. In addition, supplemental access tube 22 is configured to be placed in fluid communication with an instrument, such as a catheter. Supplemental access tube 22 can be used to introduce fluids or medical devices into the body of a patient. It can be appreciated that an adaptor employing valve apparatus 16 may have various other configurations in order to carry out an intended function, including a configuration employing a tubular body without a supplemental access tube or with a plurality of supplemental access tubes.

Tubular body 12 is coupled in fluid communication with a valve body 26 of valve apparatus 16. Locking nut 32 is rotatably coupled to valve body 26 as shown in FIG. 1.

FIG. 1 also depicts a proximal, funnel shaped portion 44 of an introducer 24 of valve apparatus 16. Introducer 24 is movably coupled to locking nut 32, which is movably a coupled to valve body 26, and will be discussed in greater detail below. Introducer 24 moves between a first position, shown in FIG. 1, in which the proximal funnel shaped hub end 44 is positioned away from locking nut 32 and a second position in which funnel shaped proximal hub end 44 is positioned adjacent locking nut 32. Valve apparatus 16 is further shown in exploded views in FIGS. 2 and 3.

Figure 2:
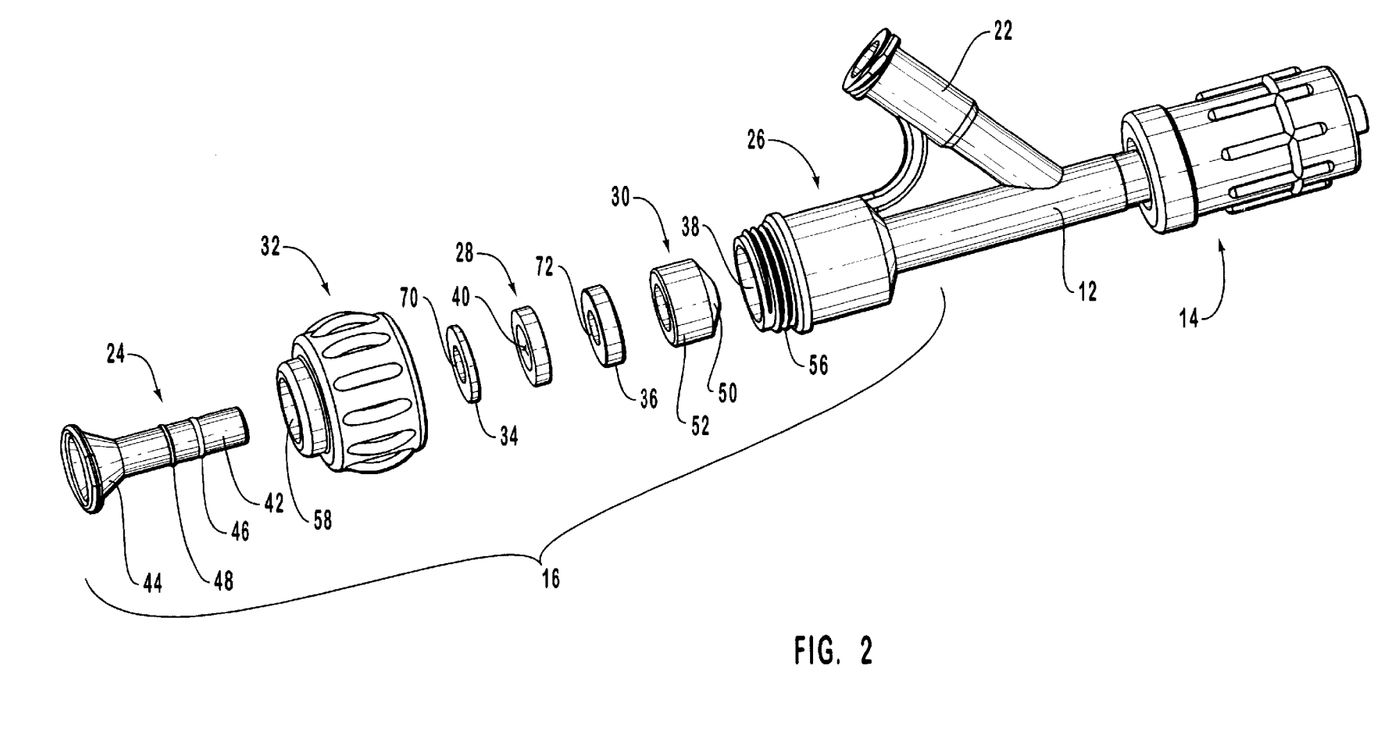
FIG. 2 is a perspective view of the adaptor of the present invention featuring the valve apparatus in an exploded view.
Figure 3:
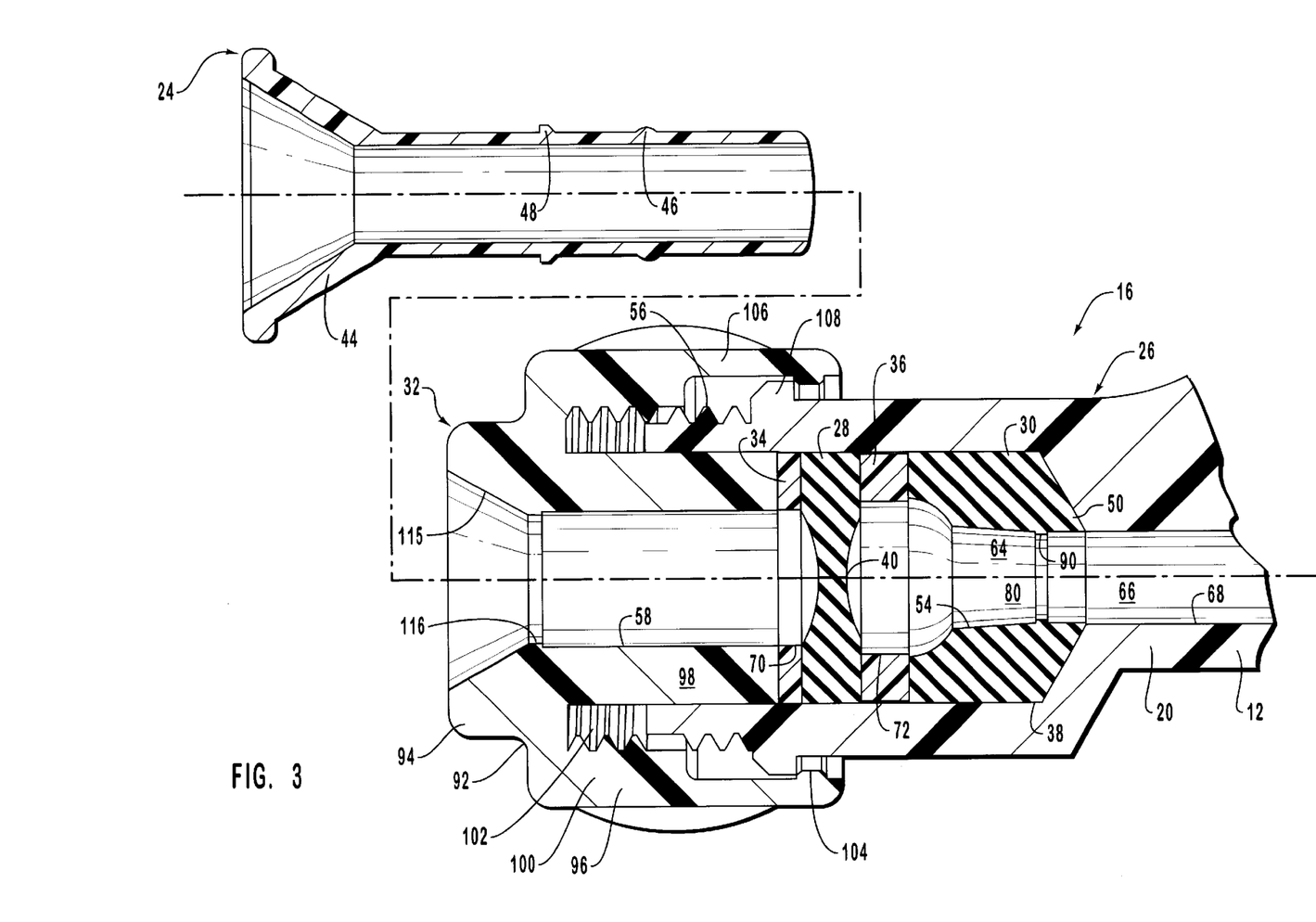
FIG. 3 is a view of the valve apparatus of the present invention with the introducer exploded from the body of the valve.

As shown in FIGS. 1–3, valve apparatus 16 includes (i) valve body 26 having an interior surface 38 defining a lumen therethrough; (ii) a resilient seal 28; (iii) introducer 24 for selectively opening resilient seal 28; (iv) compressible seal 30, and (v) a hollow, rotating locking nut 32 for selectively compressing seal 30. Washers 34, 36 are also shown.

The exterior surfaces of resilient and compressible seals 28, 30 and washers 34, 36 are configured to mate with a corresponding portion of the interior surface 38 of valve body 26. Washers 34, 36 are preferably located on opposing sides of resilient seal 28. One function of washer 34 is to prevent twisting of resilient seal 28 as locking nut 32 is advanced with respect to compressible seal 30.

In the embodiment of FIGS. 1–3, valve body 26 is integrally coupled in fluid communication to adaptor tubular body 12. In another embodiment, valve body 26 or another valve body useful in the present invention is removably or non-removably affixed to a tubular body. Body 26 is one embodiment of a structure capable of performing the function of a means for providing a lumen therethrough. It can be appreciated that various other embodiments of a means for providing a lumen therethrough may be equally effective in carrying out the intended function thereof.

With reference to FIGS. 2–3, resilient seal 28 is configured for preventing loss of body fluids from the lumen of the valve body 26. In use, resilient seal 28 is disposed within interior surface 38 of body 26. Seal 28 has a cylindrically shaped, thin, flexible membrane body having opposing recessed side surfaces. The resilient seal may have other configurations such as being semi-spherically shaped, flat, or elliptical while providing the intended function thereof. The membrane may be a material selected from the group consisting of silicon rubber and other elastomer materials, for example.

An aperture 40 (closed in FIGS. 2 and 3) extends through the sides of seal 28. An elongate instrument, such as a catheter or guide wire, can be disposed through aperture 40 of seal 28. Aperture 40 preferably has an inner diameter which is smaller than the outer diameter of introducer 24, thereby causing aperture 40 to seal about introducer 24 when introducer 24 is disposed therethrough.

In the embodiment of FIG. 2, resilient seal 28 is a tricuspid slit valve. When resilient seal 28 is disposed in interior surface 38 of body 26, seal 28 is capable of preventing loss of body fluids from body 26 and seals around the exterior surface of an elongate instrument residing within valve apparatus 16.

Resilient seal 28 assumes an open position when a force such as introducer 24 is directed against resilient seal 28. Resilient seal 28 assumes a normally closed position when not subjected to a force directed against resilient seal 28. Resilient seal 28 is one embodiment of structure capable of performing the function of a resilient sealing means, disposed in valve body 26 for preventing loss of body fluids from the lumen of valve body 26. Seal 28 has a selectively openable aperture 40. Other examples of such a resilient sealing means include single slit valves, valves having more than three slits, or other resilient valves known in the art or yet to be produced.

Introducer 24 comprises an elongate hollow tubular body 42 having a funnel-shaped proximal hub 44 coupled thereto and in fluid communication therewith. Hub 44 contacts a mating portion of interior surface 58 of locking nut 58, which acts as a stop when introducer 24 is moved from a first position to a second position.

First and second annular ribs 46, 48 extend about tubular body 42. Ribs 46 and 48 are each examples of guide means for guiding introducer 24 in a straight, longitudinal, reciprocating path within locking nut 32. However, the introducer of the present invention may have a variety of different shapes and configurations, any of which enable the introducer to open resilient seal 28 when the introducer is inserted therethrough. Tubular body 42 of introducer 24 has sufficient size to be inserted through resilient seal 28 and to thereby maintain resilient seal 28 in an open position. The insertion of tubular body 42 through seal 24 maintains tubular body 42 within seal 28 until introducer 24 is moved therefrom.

With continued reference to FIGS. 2–3, compressible seal 30 has a hollow conical distal end 50 extending from a hollow, cylindrical proximal end 52. Compressible seal 30 has an interior surface 54 defining an opening therethrough. Distal end 50 is configured to mate within a corresponding distal portion of interior surface 38 of valve body 26. It can be appreciated that the exterior surface of hollow compressible seal 30 may have other configurations as long as both compressible seal 30 and interior surface 38 of body 26 are configured to cooperate.

Compressible seal 30 responds to compressive forces exerted thereon to seal valve 16. When compressive force is exerted on compressible seal 30, a portion of compressible seal 30 moves radially inward to form a progressively tighter seal around an elongate instrument such as a catheter or guide wire that is disposed in compressive seal 30. The amount of compressive force that is being exerted on compressible seal 30 can be incrementally adjusted so that a seal is formed or maintained around the catheter or guide wire while still allowing the catheter or guide wire to be repositioned or even removed without having to remove all of the compressive force acting on the compressible seal. Also, because of the adjustability of seal 30 it is possible to dispose elongate medical instruments having a variety of different diameters therethrough.

Hollow, rotatable locking nut 32 is configured to selectively thread onto first engagement threads 56 of valve body 26 and to selectively compress compressible seal 30. Rotatable locking nut 32 has an interior surface 58 defining an opening therethrough. In operation, introducer 24 reciprocates between first and second positions within rotating locking nut 32 and is slidably coupled to interior surface 58 thereof.

FIG. 3 depicts a partially assembled cross sectional view of valve apparatus 16 and a portion of tubular body 12. Introducer 24 is exploded from valve body 26 in FIG. 3. As shown, body 26 has a lumen 64 extending therethrough defined by interior surface 38. Lumen 64 is in fluid communication with a lumen 66 defined by an interior surface 68 of tubular body 12. As shown, in an assembled embodiment, compressible seal 30 is positioned in a mating relationship within interior surface 38 of valve body 26. Washer 36 is positioned adjacent compressible seal 30 and resilient seal 28 is positioned adjacent washer 36. Washer 34 is positioned on an opposing side of seal 28 within body 26. Hollow, rotatable locking nut 32 is movably coupled to body 26 and substantially surrounds tubular body 42 of introducer 24, which is movably coupled to nut 32. Resilient seal 28 is closed while compressible seal 30 is open in FIG. 3.

Compressible seal 30 includes an opening 80 therethrough which communicates with lumen 64 of body 26 when the seal 30 is in an open position. Compressible seal 30 selectively opens and closes opening 80 in response to a compressive force exerted on seal 30. Seal 30 assumes a normally open position when not subjected to said compressive force. Seal 30 responds to compressive force so as to selectively and progressively reduce the size of opening 80.

As further shown in FIG. 3, a raised annular portion, such as by way of example and not limitation, raised annular sealing rib 90, is integrally formed on interior surface 54 of compressible seal 30. Raised annular rib 90 may have various other configurations and perform the functions thereof equally effectively. By way of example and not limitation, a raised annular rib of the present invention may be shaped as semi-spherical, half an ellipse, rounded, semi-circular, rectangular, half an octagon, or various other shapes.

Rib 90 is configured to allow an elongate instrument accessing lumen 64 to be repositioned or removed while still maintaining a seal capable of preventing substantially all loss of body fluids beyond compressive seal 30 and without releasing all of the compressive force acting on compressive seal 30. Other embodiments including alternative structures capable of performing the function of such a rib may be equally effective in carrying out the intended function thereof.

Compressible seal 30 preferably comprises a deformable, resilient material which allows compressible seal 30 to compress in response to a compressive force and either form a seal with itself or form a seal around an elongate instrument positioned through opening 80. The material comprising compressible seal 30 should also be sufficiently resilient to enable compressible seal 30 to independently conform back to its original configuration when the compressive force is removed. The preferred material for tubular compressible seal 30 is silicon rubber. It is, however, contemplated that compressible seal 30 may be composed of other kinds of conventional rubbers and elastomeric materials. The exterior surface of compressible seal 30 can be coated with an oil to prevent the surface from sticking to body 26 as locking nut 32 is retracted.

Compressible seal 30 is one embodiment of structure capable of performing the function of a compressible sealing means disposed within body 26 for selectively sealing and unsealing lumen 64 of body 26 in response to a compressive force exerted on seal 30.

With continued reference to FIG. 3, rotatable locking nut 32 comprises an end wall 92 on proximal end 94 thereof; an outer, annular side wall 96 extending integrally and distally from end wall 92; and an inner, hollow, annular neck 98 extending integrally and distally from end wall 92. Extending from a proximal end 100 of annular side wall 96 is a set of second engagement threads 102 configured for rotational, threaded engagement with first engagement threads 56 on the proximal end of body 26.

Sidewall 96 also has an annular ridge 104 extending from distal end 106 thereof which, during assembly, slips over an annular ridge 108 on the proximal end of body 26 and prevents rotatable locking nut 32 from being inadvertently threaded off body 26. Thus, in order to remove rotatable locking nut 32 from body, locking nut 32 must be pulled from body 26 over ridge 108 such that ridge 104 is pulled over ridge 108.

In use, nut 32 may be selectively rotated relative to body 26 such that neck 98 proceeds distally to thereby compress against seals 28 and 30, causing compressible seal 30 to close. Upon desiring to open compressible seal 30, nut 32 is rotated proximally, thereby opening seal 30.

Neck 98 is thus configured to selectively advance within lumen 64 to thereby exert force against compressible seal 30. By selectively rotating nut 32, neck 98 is selectively advanced. First engagement threads 56 and second engagement threads 102 serve collectively as an example of means for movably coupling neck 98 to the proximal end of body 26 and for selectively advancing neck 98 into lumen 64. In another embodiment (not shown) of such means for movably coupling a neck to the proximal end of a valve body, the threads on the body are internal threads engaged by externally extending threads coupled to the neck.

Neck 98 selectively advances within lumen 64 against washer 34 (or directly against resilient seal 28 in an embodiment (not shown) in which washer 34 is not employed within body 26). The advancement of neck 98 into lumen 64 compresses seal 30 within lumen 64, projecting interior surface 54 of compressible seal 30 radially inward, thereby constricting opening 80. Simultaneously, compressible seal 30 compresses radially outwardly against interior surface 38 of body 26 so as to form a seal with interior surface 38 of body 26.

Interior surface 58 of nut 32 expands radially outward at a proximal end 94 thereof to form an enlarged receiving mouth 115 for receiving funnel shaped hub end 44 of introducer 24, thereby stopping introducer 24 as introducer 24 is moved to the second position. In one embodiment, as hub 44 contacts mouth 115, the opposing distal end of introducer 24 extends longitudinally far enough to be close to seal 30 or to contact seal 30 without extending through opening 80, so as to provide a smooth transition for a medical instrument moving through the interior surface of introducer 24 into interior surface 54 of seal 30.

An annular ridge 116 projects inwardly from interior surface of neck 98. Ridge 116 engages ridge 48 of introducer 26 when introducer 24 is moved to the first position as shown in FIG. 4, acting as a stop to prevent introducer from being moved out of nut 32.

Rotatable locking nut 32 is one example of structure capable of performing the function of a compressing means movably coupled to body 26 for selectively increasing and decreasing compressive force on compression seal 30. The compression force is increased when nut 32 is rotated in one direction relative to body 26 and is gradually released when nut 32 is rotated in the opposite direction relative to body 26. Various embodiments of structure capable of performing the function of such a compressing means are equally effective in carrying out the intended function thereof.

To facilitate slippage between locking nut 32 and washer 34, washer 34 may be made of a relatively rigid material having a relatively low coefficient of friction, such as Delrin or polytetrafluorethylene, or more commonly known as Teflon®. To assist in rotational slipping between neck and washer 34 and to provide a smoother interaction between the components within valve apparatus 16, a small quantity of oil or other lubrication, such as medical grade silicone oil, can be used to lubricate the interactive components of valve apparatus 16. Washer 36 also preferably comprises a Teflon® or Delrin material.

Figure 4:
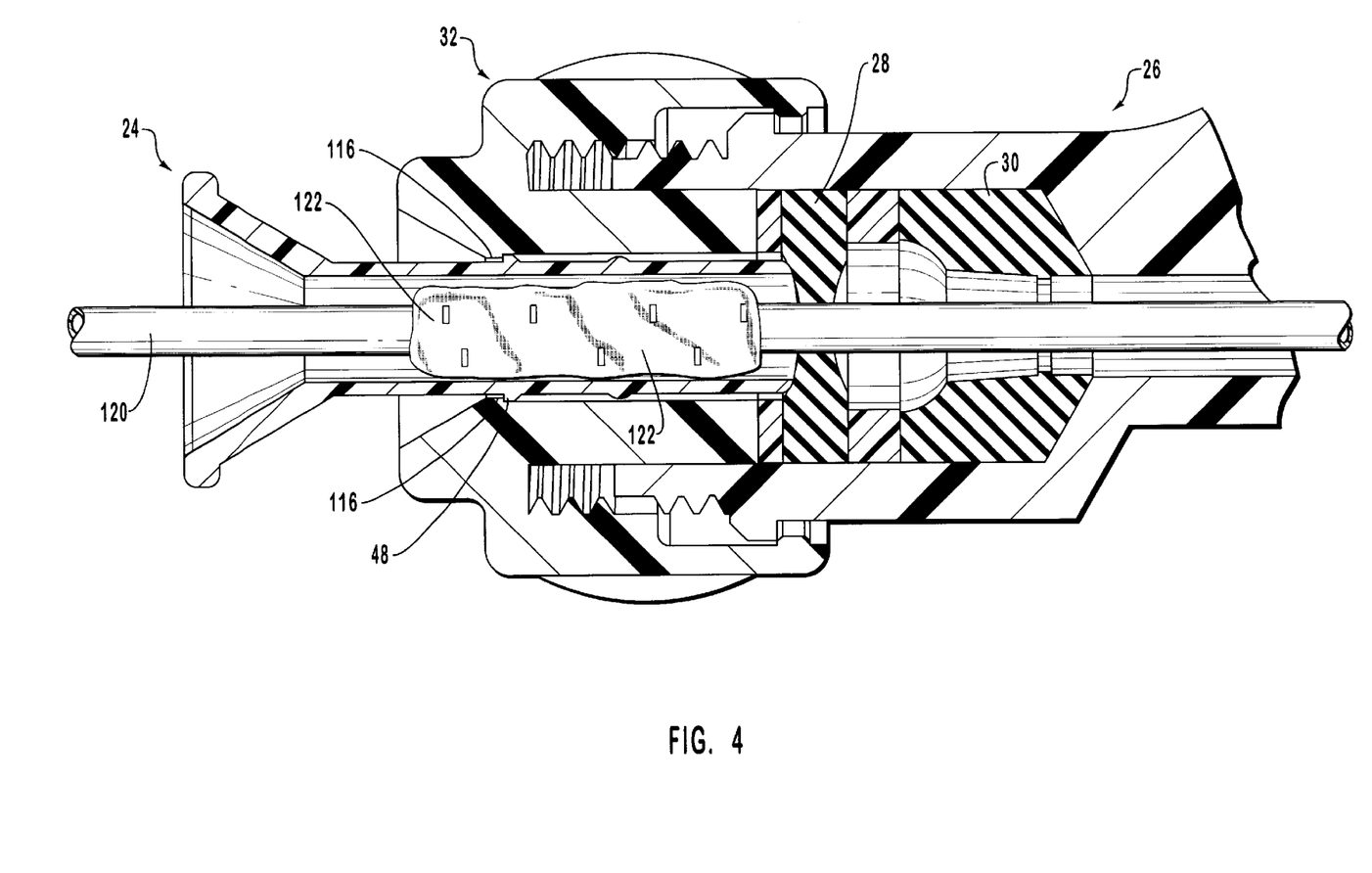
FIG. 4 is a view of the valve apparatus of FIG. 3 with the introducer movably coupled to the valve body in a first position and with an elongate medical instrument positioned in the valve. The resilient seal of the valve is closed about the medical instrument.

FIG. 4 depicts assembled adaptor 10 with an elongate member 120 disposed therein. This design elegantly combines the advantages of an adjustable, compressible seal and an integral, introducer which slides within a rotating locking nut. Introducer 24 is rotatably coupled within nut 32. Seal 28 is disposed about an exterior surface of member 120, forming a seal around elongate member 120. Seal 28 is configured to prevent loss of fluids beyond seal 28 while seal 30 is open and while the position of elongate member 120 is adjusted within valve apparatus 16.

Figure 5:
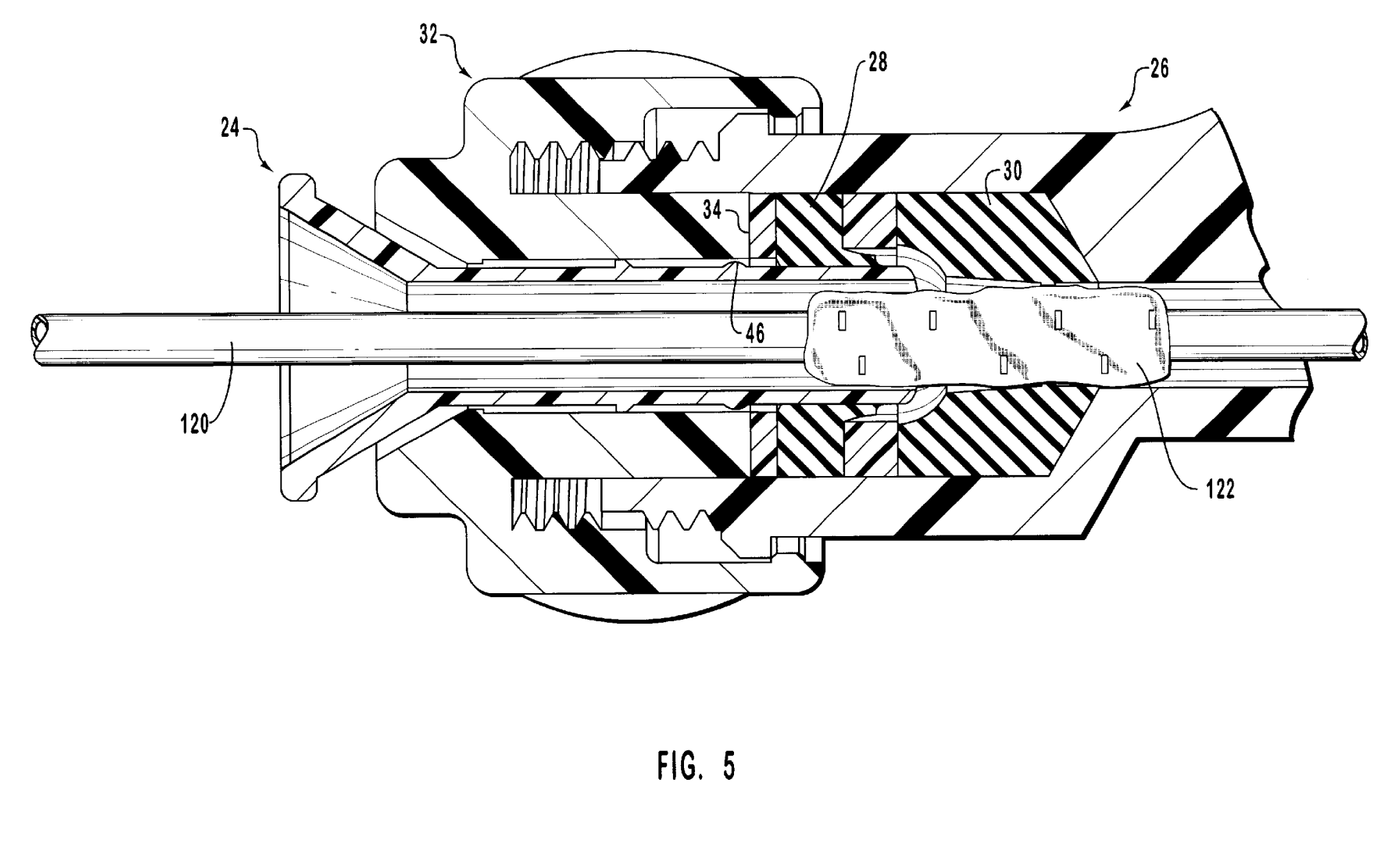
FIG. 5 is a view of the device of FIG. 4 with the introducer in a second position, wherein the resilient seal of the valve is opened by the introducer and a medical instrument is being moved through the resilient and compressible seals without damaging the medical instrument.

A first position of introducer 24 is shown in FIG. 4. A second position of introducer 24 is shown in FIG. 5. In the embodiment of FIG. 5, introducer 24 is disposed through resilient seal 28, thereby opening seal 28. Once seal 28 is opened, stent portion 122 or another portion of elongate instrument 120 can be readily extended through seal 28 and seal 30 without being damaged, as shown. Introducer 24 of FIG. 5 can be moved further toward seal 30 to reduce or eliminate any gap between introducer 24 and seal 30 so as to provide a smooth transition for instrument 120, stopping when hub 44 contacts mouth 115.

As one advantage of the present invention, in one embodiment, upon moving introducer 24 to the second position in which introducer 24 is extended through seal 28, introducer 24 is maintained in the second position by the gripping force of seal 28 upon introducer 24. A practitioner can then conveniently extend an elongate instrument through introducer 24 while introducer 24 is locked in the second position by resilient seal 28. The practitioner can then selectively remove introducer 24 from the second position when desired by pulling introducer 24 out of seal 28. Resilient seal 28 serves as an example of means for selectively locking introducer 24 in the second position.

Introducer 24 is one example of an opening means for selectively opening the resilient sealing means. However, a variety of different introducers can act as opening means for selectively opening the resilient sealing means, such as other tubular members, for example. A variety of other tubular members may be employed having a variety of different shapes and sizes. For example, it is not necessary to employ a funnel shaped member at the end of the introducer, although the funnel shaped member 44 of the present invention provides a convenient fit with rotating locking nut 32 and directs elongate members along the appropriate, desired path within introducer 24. It is possible to move introducer 24 into the second position by pressing against funnel shaped member 44 of introducer 24. It will also be appreciated that introducer 24 may be movably coupled to the locking nut 32 in a variety of different manners.

Figure 6:
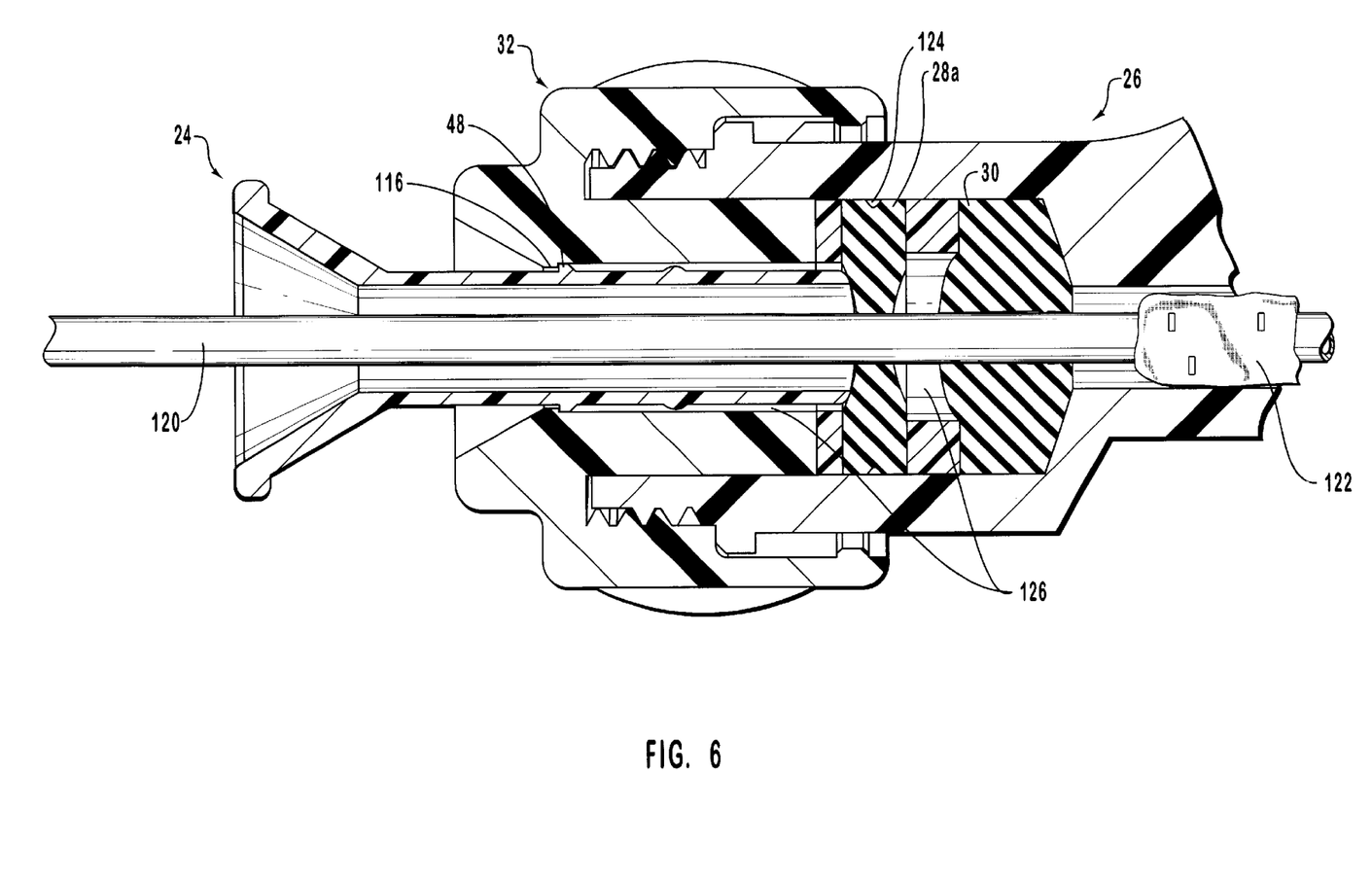
FIG. 6 is a view of the device of FIG. 5 with a stent of a medical instrument moved through the valve and with the resilient seal and the compressible seal closed about an exterior surface of the medical instrument. An alternate resilient seal is shown.

With reference now to FIG. 6, following the extension of any desired portion of elongate member 120, such as a stent portion 122, through resilient seal 28a and through opened, compressible seal 30, it is possible to then close compressible seal 30 by rotating locking nut 32 distally. By so closing compressible seal 30, it is possible to seal the exterior surface of elongate member 120 thereby preventing fluid from being expelled through valve 16.

According to another method of adjusting the position of member 120, compressible seal 30 is not completely closed but is closed far enough such that annular sealing rib 90 is disposed against the exterior surface of member 120 thereby allowing movement of member 120.

Also as shown in FIG. 6, optional resilient seal 28a is another embodiment of a resilient sealing means, disposed in valve body 26 for preventing loss of body fluids from the lumen of valve body. Resilient seal 28a features an annular groove 124.

Tubular body 12, valve 16, access tube 22, and introducer 24 may comprise a clear, transparent or translucent polycarbonate plastic. Such a plastic material allows for relatively easy molding, moderate flexibility, and the ability to see the internal components and operation of the adapters. Of course, alternative types of conventional plastics can also be used depending on one's taste and the intended use of a particular adaptor.

In one embodiment, introducer 24 is slightly tinted, such as with a blue colorant, for aesthetic purposes and to distinguish it from a clear nut 32 and body 26. Also in one embodiment, valves 28, 30 are in the form of a color, such as blue for aesthetic purposes.

Valve apparatus 16 is an example of a valve system comprising (i) a valve assembly; and (ii) an introducer (e.g., introducer 24) movably coupled to the valve assembly. The valve assembly comprises, for example, (i) a valve body, such as body 26; (ii) a compressible seal, such as seal 30, a resilient seal, such as seal 28, and (iv) a locking nut, such as nut 32.

The interior surface 38 of valve body 26 defines a passageway, i.e., lumen 64. Valve body 26 thus serves as an example of means for providing a passageway 64 therethrough. Seals 28 and 30 selectively seal passageway 64.

In addition, the interior surface 58 of locking nut 32 and the portion of the interior surface 38 of valve body 26 located distally from locking nut 32 collectively define a passageway 126 (FIG. 6). Locking nut 32 and valve body 26 thus serve collectively as another example of means for providing a passageway 126 therethrough. Seals 28 and 30 selectively seal passageway 126. Introducer 24 selectively opens the resilient seal 26, which is disposed within passageway 126.

In an alternative embodiment (not shown), a valve apparatus is provided without a resilient seal located in the valve body thereof. In one such alternative embodiment, the introducer can be employed to guide an elongate member such as elongate member 120 through a proximal portion of the valve such as through a locking nut 32 before reaching the compressible seal such as seal 30. A neck of the rotating nut presses directly against a washer adjacent seal 30 or directly against seal 30 to compress seal 30. The introducer may be movable between a first position and a second position within the locking nut, for example. In a preferred embodiment, however, the introducer extends selectively through a resilient seal.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A hemostasis valve apparatus for preventing blood loss while permitting introduction of a guidewire, a catheter for placement of a stent or balloon, and similar intravascular instruments for diagnostic and interventional procedures, tile apparatus comprising:

a valve body comprising a lumen which runs therethrough for purposes of permitting a vascular instrument to be introduced into a patient's vascular system;

a first means for scaling, situated within said valve body, for forming a first normally closed valve member across the lumen of said valve body;

a second means for scaling, situated within said valve body, for forming a second normally open valve member across the lumen of said valve body, and which is selectively closeable by exertion of a compressive force thereon;

compressive means, joined to the valve body and forming an assembly therewith which together encloses the first and second means for sealing within the assembly, for selectively exerting and removing a compressive force applied to said second means for sealing so as to selectively close and open the second means for scaling about the circumference of a vascular instrument in response to the exertion and removal of said force, respectively, and introducer means for providing a protective pathway through which a vascular instrument passes unobstructed, said introducer means being slidably moveable between a first position in which the protective pathway is fully withdrawn from the first means for sealing to permit sealing across the lumen of the valve body, and a second position in which the protective pathway extends across and through the first means for sealing, movement of the introducer means and operation of the compressive means being independent of one another so that the compressive means is operable to selectively open and close the second means for sealing independent of whether the introducer means is in the first or second position, and so that the introducer means is moveable to the first or second position independent of whether the compressive means is operated to close the second means for sealing or is operated to open the second means for sealing.

2. A valve apparatus as recited in claim 1, wherein the compressive means comprises a locking nut.

3. A valve system as recited in claim 2, wherein the first means for sealing and the second means for scaling are positioned within said lumen, and wherein the first means for sealing is situated between said introducer means and said second means for sealing.

4. A valve system as recited in claim 1, wherein the introducer means is telescopically coupled to the compressive means.

5. A valve as recited in claim 1, wherein the first means for scaling comprises a slit valve.

6. A valve as recited in claim 1, wherein the compressive means comprises a rotatable locking nut which has an opening therein and wherein the introducer means is telescopically situated within said opening so as to selectively reciprocate within the opening.

7. A apparatus as recited in claim 1, further comprising means for selectively locking the introducer means in the second position.

8. A hemostasis valve apparatus for preventing blood loss while permitting introduction of a guidewire, a catheter for placement of a stent or balloon, and similar intravascular instruments for diagnostic and interventional procedures, the apparatus comprising:

a valve body comprising a lumen which runs therethrough for purposes of permitting a vascular instrument to be introduced into a patient's vascular system;

a normally closed resilient seal, situated within said valve body across the lumen of said valve body;

a normally open compressible seal, situated within said valve body across the lumen of said valve body, and which is selectively closeable when deformed by exerting a compressive force on the compressible seal;

a rotatable locking nut, joined to the valve body and forming an assembly therewith which together encloses the resilient and the compressible seals within the assembly, the locking nut being rotatable about the valve body to selectively exert and remove a compressive force applied to said compressible seal so as to selectively close and open the compressible seal about the circumference of a vascular instrument in response to the exertion and removal of said force, respectively; and an elongated, hollow introducer through which a vascular instrument passes unobstructed, the introducer being telescopically joined to said rotatable locking nut so as to form part of said assembly, and said introducer being slidably moveable between a first position in which the introducer is fully withdrawn from the resilient seal to permit closure and sealing by the resilient seal, and a second position in which a portion of the introducer extends across and through the normally closed resilient seal, movement of the introducer and movement of the rotatable locking nut being independent of one another so that the locking nut is moveable to selectively open and close the compressible seal independent of whether the introducer is in the first or second position, and so that the introducer is movable to the first or second position independent of whether the locking nut is rotated to close the compressible seal or is rotated to open the compressible seal.

9. A valve apparatus as recited in claim 8, wherein the resilient and compressible seals are located within the valve body.

10. A valve as recited in claim 8, wherein the introducer is telescopically moveable within the locking nut.

11. A valve as recited in claim 8, wherein the introducer comprises a tubular body and a funnel-shaped hub coupled to and in fluid communication with the tubular body.

12. A valve as recited in claim 8, wherein the locking nut is rotatably coupled to the body and wherein the introducer is movably coupled to the locking nut and reciprocates back and forth within an opening of the locking nut.

13. An apparatus as recited in claim 8 wherein the resilient seal comprises means for selectively locking the introducer in the second position.

14. A hemostasis valve apparatus for preventing blood loss while permitting introduction of a guidewire, a catheter for placement of a stent or balloon, and similar intravascular instruments for diagnostic and interventional procedures, the apparatus comprising:

a valve body comprising a lumen which runs therethrough for purposes of permitting a vascular instrument to be introduced into a patient's vascular system;

a sealing means, situated within said valve body, for forming a normally open valve member across the lumen of said valve body, and which is selectively closeable by exertion of a compressive force thereon;

compressive means, joined to the valve body and forming an assembly therewith which together encloses the means for sealing within the assembly, for selectively exerting and removing a compressive force applied to said means for sealing so as to selectively close and open the means for sealing about the circumference of a vascular instrument in response to the exertion and removal of said force, respectively; and introducer means for providing a protective pathway through which a vascular instrument passes unobstructed, said introducer means being slidably moveable between a first position in which the protective pathway is fully withdrawn from the sealing means, and a second position in which the protective pathway extends essentially up to but not through the sealing means, movement of the introducer means and operation of the compressive means being independent of one another so that the compressive means is operable to selectively open and close the sealing means independent of whether the introducer means is in the first or second position, and so that the introducer means is moveable to the first or second position independent of whether the compressive means is operated to close the scaling means or is operated to open the sealing means; and means for selectively locking the introducer means in the second position.

15. A valve as described in claim 14, further comprising a second sealing means, situated within said valve body, for forming a normally closed valve member across the lumen of said valve body, said second scaling means being positioned between said introducer means and said sealing means for forming a second normally opened valve member.

16. A valve apparatus as defined in claim 15 wherein said second sealing means is comprised of a resilient membrane having at least one slit formed in the membrane, and wherein the said at least one slit provides the means for selectively locking the introducer means in the second position.

17. A hemostasis valve apparatus for preventing blood loss while permitting introduction of a guidewire, a catheter for placement of a stent or balloon, and similar intravascular instruments for diagnostic and interventional procedures, the apparatus comprising:

a valve body comprising a lumen which runs therethrough for purposes of permitting a vascular institute to be introduced into a patient's vascular system, a normally open compressible seal, situated within said valve body across the lumen of said valve body, and which is selectively closeable when deformed by exertinig a compressive force on the compressible seal;

a rotatable locking nut, joined to the valve body and forming an assembly therewith which together encloses the compressible seal within the assembly, the locking nut being rotatable about the valve body to selectively exert and remove a compressive force applied to said compressible seal so as to selectively close and open the compressible seal about the circumference of a vascular instrument in response to the exertion and removal of said force, respectively; and an elongated, hollow introducer through which a vascular instrument passes unobstructed, the introducer being telescopically joined to said rotatable locking nut so as to form part of said assembly, and said introducer being slidably moveable between a first position in which the introducer is withdrawn away from the compressible seal, and a second position in which the introducer is inserted so as to extend essentially up to the opening of the normally open compressible seal, movement of the introducer and movement of the rotatable locking nut being independent of one another so that the locking nut is movable to selectively open and close the compressible seal independent of whether the introducer is in the first or second position, and so that the introducer is movable to the first or second position independent of whether the locking nut is rotated to close the compressible seal or is rotated to open the compressible seal, and means for selectively locking the introducer in the second position.

18. A valve apparatus as defined in claim 17, further comprising a normally closed resilient seal, situated within said valve body across the lumen of said valve body, and located between said hollow introducer said the normally open compressible seal.

19. A valve apparatus as defined in claim 18 wherein the normally closed resilient seal is comprised of a resilient membrane and at least one slit formed in the membrane, and wherein said at least one slit serves as the means for selectively locking the introducer in the second position.

* * * * *

UNITED STATES PATENT AND TRADEMARK OFFICE
CERTIFICATE OF CORRECTION

PATENT NO. : 6,287,280 B1
DATED : September 11, 2001
INVENTOR(S) : Fred P. Lampropoulos and Brian Stevens It is certified that error appears in the above-identified patent and that said Letters Patent is hereby corrected as shown below:

<u>Column 11,</u>
Line 21, change "scaling" to -- sealing --
Line 46, change "scaling" to -- sealing --
Line 54, change "scaling" to -- sealing --

<u>Column 14,</u>
Line 3, change "exertinig" to -- exerting --
Line 30, change "seal," to -- seal; --

Signed and Sealed this

Eleventh Day of June, 2002

*Attest:*

*Attesting Officer*

JAMES E. ROGAN
*Director of the United States Patent and Trademark Office*